United States Patent [19]

Forssmann et al.

[11] Patent Number: 4,940,050

[45] Date of Patent: Jul. 10, 1990

[54] DEVICE FOR ENSURING THE PROPER POSITIONING OF ELECTRODES IN A LITHOTRIPTER

[75] Inventors: Bernd Forssmann, Germering; Wolfgang Hepp, Immenstaad; Gerold Heine, Uhldingen-Muehlhofen; Gustav Sell, Immenstaad; Hendrik Zech, Ueberlingen, all of Fed. Rep. of Germany

[73] Assignee: Dornier Medizintechnik GmbH, Freidrichshafen, Fed. Rep. of Germany

[21] Appl. No.: 262,143

[22] Filed: Oct. 21, 1988

Related U.S. Application Data

[63] Continuation of Ser. No. 917,854, Oct. 14, 1986, abandoned.

[30] Foreign Application Priority Data

Oct. 11, 1985 [DE] Fed. Rep. of Germany ....... 3536271

[51] Int. Cl.[5] .............................................. A61B 17/22

[52] U.S. Cl. .................................. 128/24 A; 606/128; 340/686

[58] Field of Search ............ 128/328, 24 A; 367/147; 340/654, 686; 606/127, 128

[56] References Cited

U.S. PATENT DOCUMENTS

| | | | |
|---|---|---|---|
| 3,896,280 | 7/1975 | Blake | 340/686 |
| 3,986,165 | 10/1976 | MacIntyre | 340/686 |
| 4,162,491 | 7/1979 | Gochis | 340/654 |
| 4,296,410 | 10/1981 | Higgs et al. | 340/686 |
| 4,608,983 | 9/1986 | Muller et al. | 128/328 |
| 4,662,375 | 5/1987 | Hepp et al. | 128/328 |
| 4,669,465 | 6/1987 | Moore et al. | 128/303.1 |

*Primary Examiner*—Ruth S. Smith

*Attorney, Agent, or Firm*—Ralf H. Siegemund

[57] ABSTRACT

In an arrangement for the generation and focussing of shock waves for purposes of comminution of concrements, wherein the generation is provided by a pair of electrodes, and the focussing is provided by a rotational ellipsoid; the electrodes extend from a sleeve being inserted in the body of the ellipsoid such that the electrodes center on one of the two focal points of the rotational ellipsoid; a positioning device for the electrodes includes a position indicator on the electrode sleeve such as a metal or optical marking on a mechanical actuator having a highly accurately predetermined positional relation to the electrodes; a position sensor on the body of the rotational ellipsoid has a highly accurately determined position in relation to the first focal point; and a circuit is connected to the position sensor to provide a audible and/or visible representation if, and only if, the position indicator has an accurate position related to the sensor as an indication that the electrodes are centered on the first focal point.

10 Claims, 3 Drawing Sheets

DEVICE FOR ENSURING THE PROPER POSITIONING OF ELECTRODES IN A LITHOTRIPTER

This is a continuation of co-pending application Ser. No. 06/917854 filed on Oct. 14, 1986 now abandoned.

BACKGROUND OF THE INVENTION

The present invention relates to accurately and exactly positioning electrodes inside a reflector, particularly of electrodes which are provided for generating shock waves, and which are to be positioned in a particular geometric relation inside a rotational ellipsoid, such equipment being used for contactless comminution of concrements in the body of a living being.

German patent 26 35 635 describes an electrode assembly for purposes of generating shock waves to be used for the comminution of concrements. This electrode construction has proven to be of significant practical value. The particular arrangement is such that two pin-like painted electrodes or electrode peaks face each other coaxially, and are mechanically interconnected in a cage-like holder while, of course, they are maintained electrically insulated from each other. The exact positioning of the electrode peaks has to be symmetrical to one of the two focal point of the rotational ellipsoid which is a pre-requisite for obtaining focussing of the reflected shock waves in the second focal point which, in turn, is to be located in, for example, a kidney stone. Even minute deviations in electrode positioning here are not only unfortunate but are simply unacceptable in case of application in humans for the comminution of kidney stones. Specifically, if the electrode peaks are not situated within very tight tolerances in relation to the (first) focal point, then a drop, even a significant drop of shock wave intensity, is observed in the second focal point which has been positioned on or in the kidney stone. This means that the kidney stone will not, or at best, be insignificantly damaged or comminuted.

DESCRIPTION OF THE INVENTION

It is an object of the present invention to provide improvements for the exact positioning of electrodes in a focal point of a rotational ellipsoid, so that, in fact, the triggering and release of shock waves can be restricted to situations in which, in fact, that position has been attained and is being maintained.

In accordance with the preferred embodiment of the present invention, it is proposed to use at least one electrical contact or position sensor which is arranged inside the elliptical reflector and which responds in a specific manner if, and only if, the electrodes are; in fact, in the desired position, while upon deviation from that position, the sensors fail to respond so that, in fact, a shock wave cannot be generated. Specifically it is suggested that the shock wave generating electrodes are connected to, i.e. mounted on a holder carrying a marking or an actuator having a well defined positional relation to the electrodes and cooperating with a strategically placed, in the rotational ellipsoid, sensor so that only the sensor will respond in case of exact positioning of the electrodes in the ellipsoid. An optical or acoustical indication (or both) is provided and/or a trigger circuit is released, or the like, permitting (enabling) the shock wave generation if, and only if, in fact, the desired position of the electrodes on one focal point of the ellipsoid has been attained. The shock wave generating electrodes may, for example, be provided with a nose or projecting actuator which triggers a micro switch provided on the ellipsoid. Alternatively, a metal insert or ring may be provided on the electrode holding the sleeve, cooperating with an inductive transducer which, in turn, is provided in the ellipsoid and responding to the position of that marking or ring. The ring may preferably be made of a ferro-magnetic material and the position signal, being inductively sensed, is generated in conjunction with high frequency operation.

Broadly, the marking (position establishing) on the electrode holder may be strictly local requiring insertion of the electrodes for attaining a particular axial and a particular angular position. The latter, however, is not required for the stated objective. Hence, the marking may be annular so that the insertion of the electrode holder is no longer annularly constrained. However, there is a trade-off here as an annular marking is more difficult to make at the desired axial accuracy; on the other hand, handling of the insertion is easier if the angular position is not critical, which is an important aspect when rapid uncomplicated electrode exchange is deemed highly desirable.

The electrode holder may be forced by means of a spring to the indexed position, and a second sensor responds to the spring bias, a coincidence of the two position signals triggers enabling of the shock wave generation. The time interval between the response of the first (principle) sensor and the response of the second sensor can also be measured and this value can be used for determining the bias of the spring which, in turn, is likely influential in the determination of the exact positioning of the electrode in the ellipsoid.

DESCRIPTION OF THE DRAWINGS

While the specification concludes with claims particularly pointing out and distinctly claiming the subject matter which is regarded as the invention, it is believed that the invention, the objects and features of the invention, and further objects, features, and advantages thereof will be better understood from the following description taken in connection with the accompanying drawings in which:

Proceeding now to the detailed description of the drawings, FIG. 1 illustrates a cross-section through a rotational ellipsoid 2, being, of course, a partial ellipsoid only . That ellipsoid has a first focal point F1. Two, very closely spaced peaks or points, respectively, of two electrodes 14 and 16, are positioned in a cage 12 to center, so to speak, the focal point F1 in-between them. The object, of course, is to attain and maintain that position at the highest degree of accuracy possible. Basically, the rotational ellipsoid is of the type with an arc discharge producing shock waves for kidney stone comminution and as shown, for example, in U.S. Pat. No. 3,942,531, corresponding to German Patent No. 23

Figure 1:
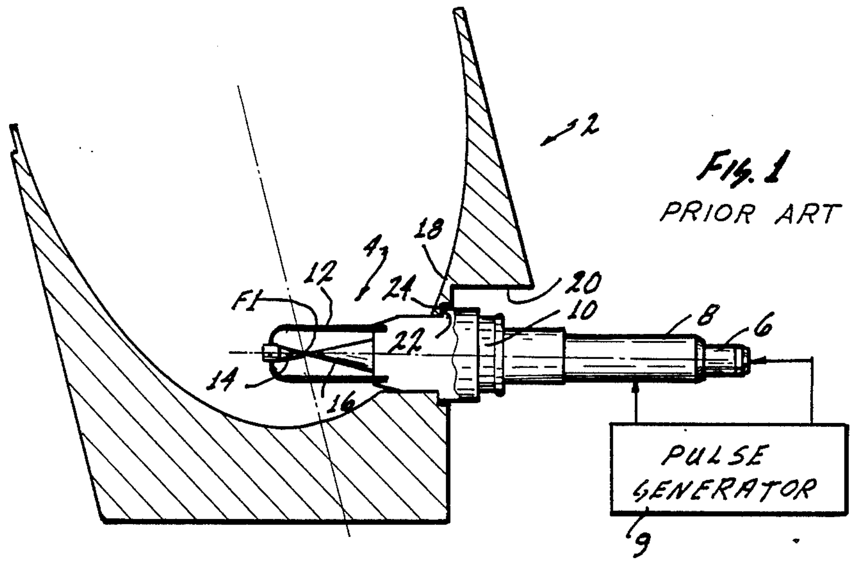
FIG. 1 PRIOR ART
FIG. 1 is a cross-section through a rotational ellipsoid with particularly positioned arc discharge electrodes for shock wave generation, including basic structural elements in relation to which the invention will be practiced.

51 247. The ellipsoid is defined as the internal surface of a body 18 which is filled with a liquid such as water.

The basic construction of the electrode assembly 4 is subject of the German Patent No. 26 35 635, but other constructions are available such as shown, for example, in U.S. Pat. No. 4,608,983. The two electrodes 14 and 16 are connected to two coaxial lines or conductors 6 and 8, respectively, which are maintained, of course, in insulated relation to each other and they are held in a housing 10 which is a cylindrical sleeve that is inserted in a bore 20 of the ellipsoid 2.

Figure 8:
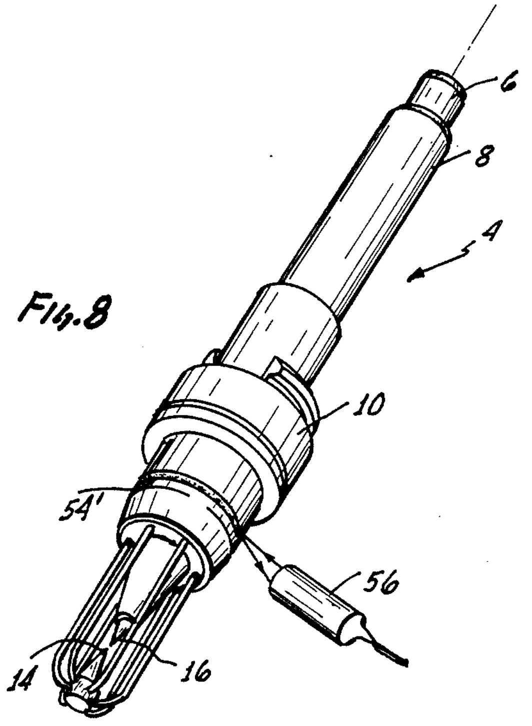
FIG. 8 is an isometric view of an electrode assembly further improved as per the specific example of FIG. 7.

Reference is also made to FIG. 8 which illustrates the configuration of the electrode assembly 4 in an isometric view. One can see particularly in greater detail the cage 12 of the electrode assembly 4. The elements 54 and 56 of that figure will be explained more fully towards the end of the specification.

Certain electric circuit elements (block 9) are connected to the electrodes 14 and 16 which generate an electric pulse in the manner known per se so that a discharge occurs across the narrow gap between the electrodes 14 and 16. The spark, of course, is produced, or better, is to be produced under all and any circumstances only if, in fact, the spark coincides with the focal point F1. Then, and only then, will a shock wave pattern be generated which, upon propagating towards the ellipsoidal wall, is reflected thereat such that it is concentrated in the second focal point (not shown) of the ellipsoid, and, of course, the concrement to be comminuted has previously been situated so that the second focal point is right in that concrement.

The cylindrical bore 20 in body 18 is provided with a step or shoulder 22, cooperating with a shoulder 24 on the sleeve 10. It can readily be seen that this way one obtains a particular position of the entire electrode structure in relation to the focal point, if sleeve 10, particularly the step or shoulder 24, on one hand, and the shoulder 22, on the other hand, are so accurate that, in fact, upon abutment of the shoulders 22 and 24, the electrodes have the desired position.

Herein, the following has to be observed. Owing to certain burn-off, it is inevitable that the peaks of the electrodes deteriorate, no matter how hard the material they are made of; the electrodes as such are a consumable item. This means that the electrode assembly 4 has to be replaced relatively frequently. This, in turn, means that, in fact, the ellipsoid body 18 with the stop 22, on one hand, and the sleeves 10 with inserted electrodes and its shoulder 24, on the other hand, are independently made, and still must meet, the accuracy requirements such that upon abutment of 22 against 24, the two electrodes 16 and 14 are centered on the focal point F1. Not only that, it has to be observed that conceivably the electrode may have to be exchanged and replaced rather rapidly that is, even during the treatment of a patient. Hence, the entire arrangement must be such that the electrode assembly with sleeve 10 should simply be pulled out and replaced by a different one, and even in that case, it must be absolutely guaranteed that, in fact, the electrodes 14 and 16 of the new electrode have their peaks right on the focal point F1. As stated, even minutest deviations here diminishes very drastically the energy concentration in the second focal point. A simple positioning of 22-abuts-24 is simply not sufficient a guarantee that the desired position is, in fact, attained.

The purpose of the following description is to describe a variety of measures by means of which the positioning, on one hand, can be improved but, on the other hand, indication is provided, and/or functions are released, such that shock wave generation will occur only when, in fact, the desired electrode position has been attained.

Figure 2:
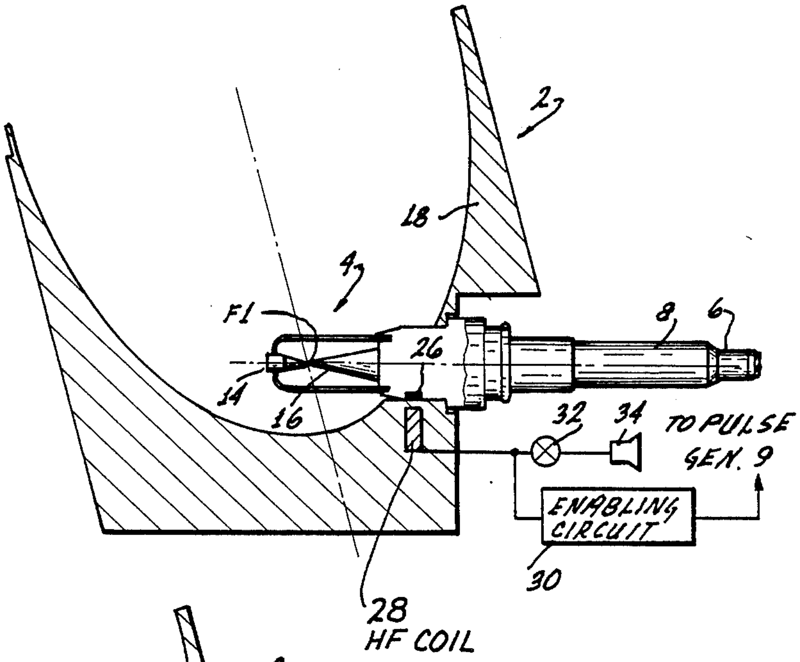
FIGS. 2 through 7 are views similar to FIG. 1, but each illustrating a different form and supplement for practicing the preferred embodiment of the invention in accordance with the best mode thereof.

Proceeding therefore, by way of example, to FIG. 2, all parts as described thus far, with reference to FIG. 1, are retained in FIG. 2. The same is actually true with regard to the other FIGS. 3 through 7. However, as a first form of practicing the invention, the electrode assembly 4, particularly the holding sleeve 10, is provided in a particular location with a small flat metallic insert 26. Presumably, the sleeve 10 is made of plastic or of a different metal, if sufficient insulation is maintained vis-a-vis the electrodes 14 and 16. The ellipsoid body 18, on the other hand, is provided at a specific location visible in the drawing with an inductive proximity switch 28, basically including a high frequency type of coil.

The arrangement now, clearly, has a double safety feature. On one hand, the sleeve 10 in relation to the electrodes 14 and 16 must be very accurately machined, as far as the relation between the location (center) of the insert 26, and the location of the shoulder 24 is concerned. On the other hand, the ellipsoid body 18 must be provided with that particular coil 28 such that its center axes has very accurate relations to the focal point Fl. Hence, there is a double safety feature; abutment of 22 against 24 and 26 must be centered vis-a-vis the axes of coil 28. Then, and only then, is a adequate signal developed by and in the .coil 28. This, in turn, means that a blocking function of an enabling circuit 30 is released. In other words, establishing the spacial relationship between the metal insert 26 and the coil 28, is a pre-requisite before the circuit 30 enables triggering of the circuit 9 which in turn provides the trigger pulse for the shock wave generator, i.e. the pulse fed to the input electrodes 14 and 16.

Reference numeral 32 refers schematically to an optical indicator, and reference numeral 34 refers schematically to an acoustic indicator, either or both can be provided such that a visible and/or audible indication is provided as an indication that, in fact, the circuit 30 has released, or permits the release of the spark gap and shock wave generation. The attending physician, therefore, simply has to observe the light 32 or listen to the sound 34, in order to know that, in fact, now the electrodes 14 and 16 are properly positioned on the focal point F1. He may then manually actually trigger the shock wave generation.

The metal plate 26 can either be magnetizable or simply be conductive so as to cooperate on an eddy current basis with the high frequency coil 28. In other words, this particular example is broadly representative of electromagnetic interaction and high frequency impedence change, when plate 26 is aligned or not with 28.

Figure 3:
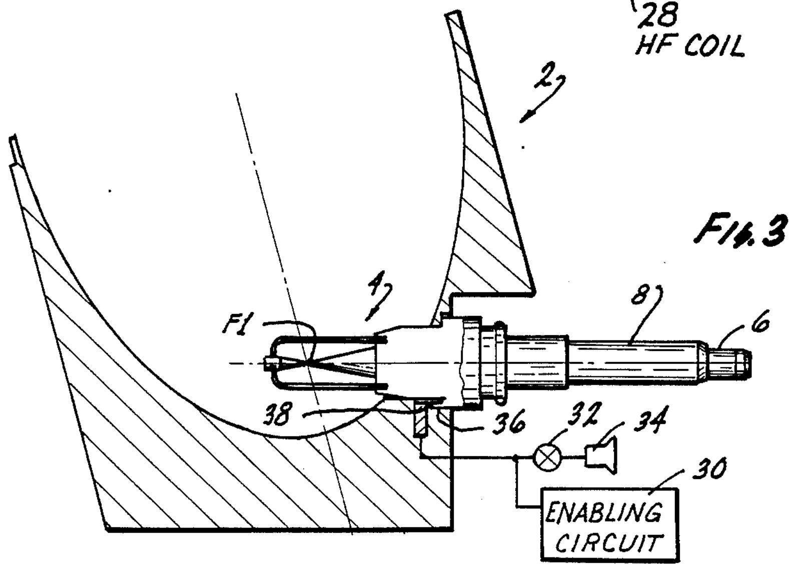

As stated, FIG. 3 shows the same elements as shown in FIG. 1, and also the blocking circuits 30, as well as the visible-audible indications 32, 34 are the same as shown in FIG. 2. In deviation from FIG. 2, now the sleeve 10 is slightly modified in that it carries a small, pin projection nose 36 or the like. This small element has a tip portion that is very accurately positioned in relationship to the shoulder 22. Reference numeral 38 in this example, is a micro switch, and it is the physical actuation of the micro switch by the nose 36 that indicates proper positioning of the electrodes 14 and 16 in relation to the focal point F1. The micro switch 38, of course, bears a very accurate position as far as the switching contact is concerned, to the focal point F1 as part of the ellipsoid equipment.

Figure 4:
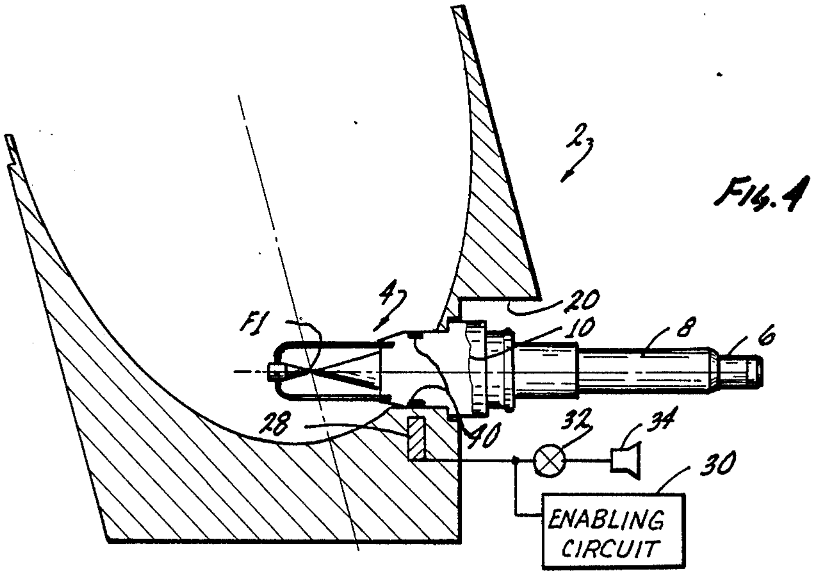

FIG. 4 is, as far as the ellipsoid equipment is concerned, similar to the embodiment shown in FIG. 2; in other words, there is a particular inductive proximity switch 28, including, and being primarily comprised of a coil with an axis that determines very accurately the lateral position for the sleeve 10. The sleeve 10, however, carries a ring 40, made of metal and/or magnetizable material This configuration establishes complete rotational symmetry of the electrode 4, at least as far as the electrodes 14 and 16 are concerned, vis-a-vis the axis of the sleeve 10. It is simply then a somewhat simplified version and facilitates insertion in bore 20, in that no particular rotational or angular position of the electrode assembly 4 has to be observed upon insertion. This particular feature considers also the aspect that, of course, the electrode assembly 4 is provided with a certain rotational asymmetry owing to the loops cage 12. However, it was found that the angular position of that cage is rather unimportant as far as the shock wave generation and propagation is concerned.

Figure 5:
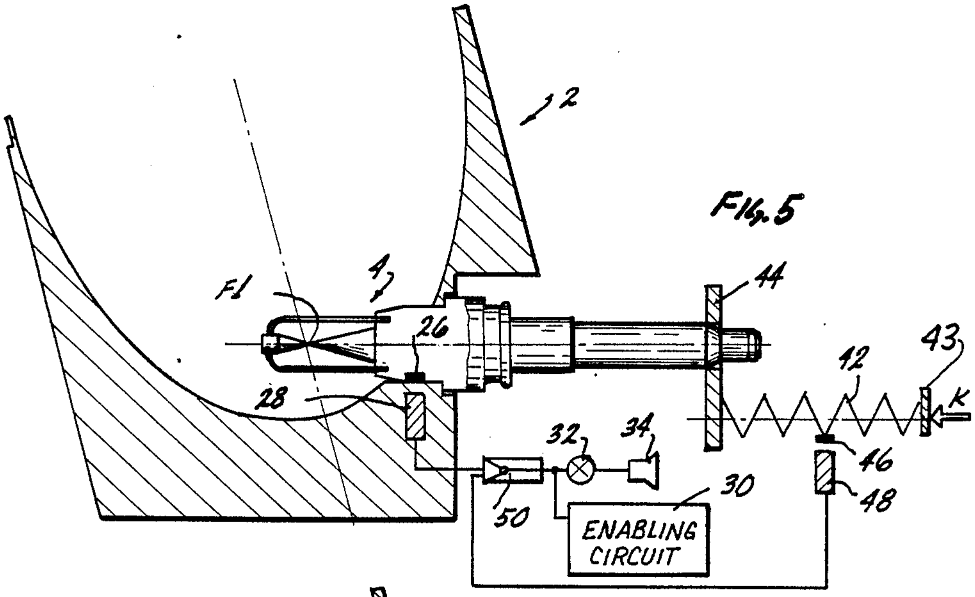
Figure 6:
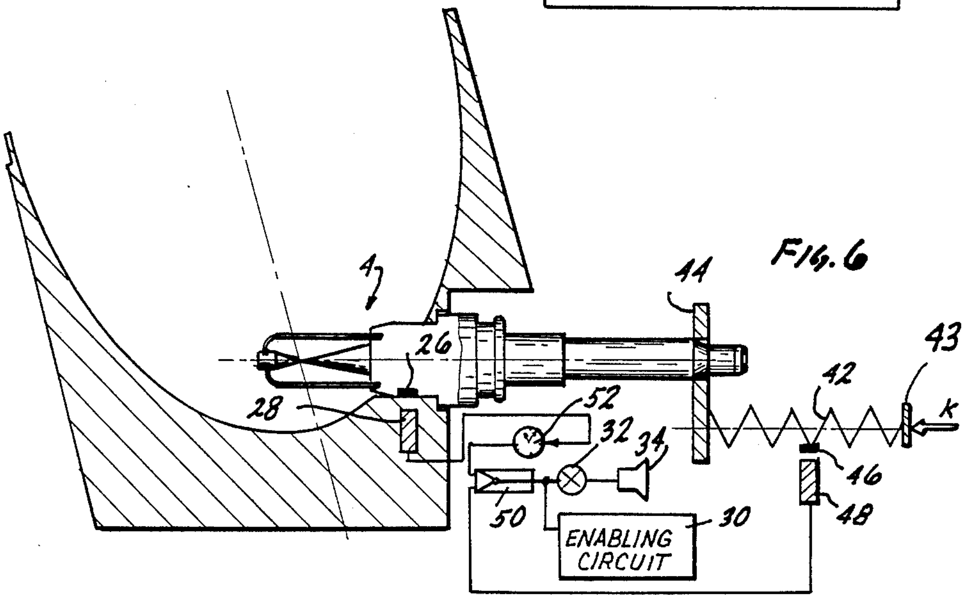

FIGS. 5 and 6 have certain common features to be explained first. Aside of the commonality that is to be traced back to FIG. 1, the electrode assembly 4 carries, in addition, a positioning plate 44. A spiral spring 42 or the like is interposed between that plate 44 and a stationary support 43. Now, the spring 42 is, for example, centrally provided with a metal disk or the like 46, which is magnetizable or non-magnetizable depending upon the configuration of a stationary transducer 48. The co-action between the transducer 48 and the plate 46 is the same as was explained above with reference to parts 26 and 28 in FIG. 2. In fact, then, this assembly 46-48 provides an indication of the relative position of the spring 42. The arrangement, as far as ellipsoid housing sensor and sleeve 10 indicator is concerned, is the same as in FIG. 2, in other words, there is also the inductive transducer 28 and the metal plate 26. The blocking circuit 30 as well as the visible and audible indication 32-34 are all as described. Now, however, in addition, a logic AND-circuit 50 has its two inputs connected such that a coincidence is necessary of a response of the transducer 28 and of a response of the transducer 48. In other words, before the release circuit 30 can be triggered, it is not only necessary that the metal plate 26 of the sleeve 10 is accurately positioned vis-a-vis the transducer 28, but it is also necessary that plate 46, indicating the spring position, is accurately positioned vis-a-vis the transducer 48. The purpose of this arrangement is to insure that not only has the desired position been attained, but proper positive action, namely spring action, maintains that position.

All these parts which have been described thus far with reference to FIG. 5 are included in the arrangement of FIG. 6. However, in addition FIG. 6 indicates schematically that a timing circuit 52 responds to any timing different in response to the transducers 28 and 48. This timing difference represents the bias of the spring 42 The release of circuit 30 is, therefore, now predicated only on a particular bias on the spring, and only if that bias is attained will the circuit 30 be released.

More specifically, as the electrode assembly 4 is pushed into position, the pickup and sensing transducer 28 will respond first. Then after the back support for spring 42 is pushed further. Since the force of a spring is usually proportional to the displacement contraction and since for a constant speed there is again proportionality in time, the delay between the responses of 28 and 46 is inductive of the spring force. During subsequent operation of the shock wave generator the spring force retaining the electrode assembly 4 in position should be constant or not below a particular minimum.

The input for gate 50 from transducer 28 is passed through a delay 52, the delay being indicative of the minimum spring force. Thus, the input for gate 50 from transducer 46 (or a differentiated-in-time output thereof) will be effective only if not earlier than the delayed response of 28. If 46 responds too early, or if 28 does not respond at all, there is some impediment and 4 is not positioned properly.

Figure 7:
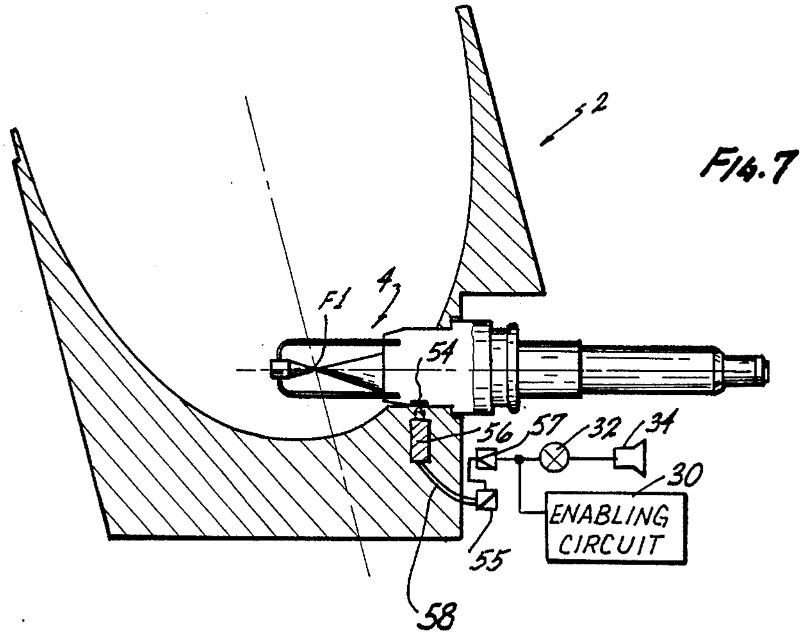

FIG. 7 indicates a still further example. Here, the particular position markings, so to speak, on the sleeve 10 is provided by a true marking 54. This marking may be provided in terms of an optical contrast markings, or as a fluorescent dot, or the like. This marking cooperates with a photoelectric transmitter/receiver 56 which in turn cooperates with a fiber optic 58 and an amplifier arrangement 55/57 coupled to said fiber optic 58.

FIG. 8 illustrates also in detail the geometric relation between the electrode assembly of FIG. 7, as already described in some respect above and the stationary equipment. Suffice it to say that FIG. 8 shows in addition a ring-like marking 54' which, again, renders the insertion of the electrode in the ellipsoid housing independent from any azimuthal constraint.

The invention is not limited to the embodiments described above, but all changes and modifications thereof, not constituting departures from the spirit and scope of the invention are intended to be included.

We claim:

1. In a lithotripter which includes a device for the generation and focussing of shock waves for purposes of comminution of concrements, the device including a pair of electrodes positioned in a rotational ellipsoid for focussing generated shockwaves, the ellipsoid having a body, said pair of electrodes extending from a holder, the holder being inserted in said body such that the electrodes center on a first one of the two focal points of the rotational ellipsoid, the improvement comprising, a positioning device for the electrodes, in the body of rotational ellipsoid and including a position sensing means mounted in the body of the rotational ellipsoid, having a highly accurate and determined position in relation to said first focal point;

a position indicating and establishing means mounted on said electrode holder such that the position indicating and establishing means has a particular, highly accurate and predetermined position in relation to said electrodes; and circuit means connected to said position sensing means to provide a signal representing an accurate position relation of alignment between the position sensing means and the position establishing means if, and only if, said position indicating and establishing means is in said accurate position relation of alignment with respect to said position sensing means, whereby said electrodes are positioned on said first focal point.

2. A lithotripter as in claim 1, and including additional circuit means responsive to said signal to provide a further signal permitting generation of a shock wave through generation of a spark gap across said electrodes if, and only if, said additional circuit means indicates establishing of said accurate position relation of alignment between said position sensing means and said position establishing means.

3. A lithotripter as in claim 1, said circuit means including means for providing an acoustic and a visible indication.

4. A lithotripter as in claim 1, wherein said position indicating and establishing means is a nose, said position sensing means is a micro-switch.

5. A lithotripter as in claim 1, wherein said position indicating and establishing means includes a metal element, said position sensing means is an inductive transducer.

6. A lithotripter as in claim 5, wherein said position indicating and establishing means further including a sleeve, said metal element being a metallic ring, so that the signal representation is provided independent from an angular position of the sleeve in the body.

7. A lithotripter as in claim 1, including spring biasing means for urging said electrode holder into said desired position.

8. A lithotripter as in claim 1, wherein the position indicating and establishing means comprises a contrasting and/or fluorescent marking, said position sensing means, comprises a photoelectric transducer.

9. A lithotripter as in claim 1, wherein said position indicating and establishing means is of annular configuration for rendering response of said position sensing means independent from the angular position of said pair of electrodes in said body.

10. A lithotripter as in claim 9, the position indicating and establishing means being a contrasting and/or flourescent marking, said sensing means being a photoelectric transducer.

* * * * *